United States Patent [19]

Ingram

[11] Patent Number: 4,902,288

[45] Date of Patent: Feb. 20, 1990

[54] IMPLANTABLE IMMUNOTHERAPY SYSTEM USING STIMULATED CELLS

[76] Inventor: Marylou Ingram, 371 Patrician Way, Pasadena, Calif. 91105

[21] Appl. No.: 804,068

[22] Filed: Dec. 3, 1985

[51] Int. Cl.$^4$ .................... A61K 9/22; A61K 35/12
[52] U.S. Cl. ............................ 604/891.1; 424/95; 424/423; 424/85.1; 424/85.8; 604/890.1
[58] Field of Search ............ 424/95, 85.1, 85.8; 435/240.2; 604/891.1

[56] References Cited

U.S. PATENT DOCUMENTS

| | | | |
|---|---|---|---|
| 4,485,096 | 11/1984 | Bell | 424/95 |
| 4,609,551 | 9/1986 | Caplan et al. | 424/95 |
| 4,645,669 | 2/1987 | Reid | 424/95 |
| 4,690,915 | 9/1987 | Rosenberg | 435/240.2 |

OTHER PUBLICATIONS

Nilsson et al.,—Chem. Abst., vol. 99, (1982), p. 118813q.
Ingram et al.—Arch. of Surg., vol. 122, (Dec. 1987), pp. 1483–1486.
Ingram et al.—J. of Biol. Response Modifiers, vol. 6, (1987), pp. 489–498.

*Primary Examiner*—Sam Rosen
*Attorney, Agent, or Firm*—Wolf, Greenfield & Sacks

[57] ABSTRACT

This invention involves treating a patient having a tumor by introducing at the area of the tumor immunologically active cells which are antagonistic to the tumor. The cells being contained in a matrix which allows for cell migration. For example the matrix can be a blood clot.

7 Claims, No Drawings

IMPLANTABLE IMMUNOTHERAPY SYSTEM USING STIMULATED CELLS

BACKGROUND

This invention comprises a system for treating a patient having a tumor to aid in eliminating or inactivating the tumor. The system also has use in healing of viral lesions. Immunologically active cells which are antagonistic to tumors have been described in the art, as for example, in U.S. Pat. No. 4,464,355 where natural killer cells are provided with the aid of Interleukin 2 (IL2). Immunologically active cells which are antagonistic to tumors include natural killer, cytotoxic T cells macrophages et al. Some have the ability to learn on proper stimulation to kill tumor cells, others including natural killer cells have a built in ability to kill tumor cells and without prior interaction with tumor cells. Certain of such cells are described in *Hospital Practice,* April, 1982 "Natural Killer Cells", R. Herberman, pages 93–103 and *Science,* Sept. 28, 1984, Volume 225, pages 1487–1489, Mule et al, "Adoptive Immunotherapy of Established Pulmonary Metastases With LAK Cells and Recombinant Interleukin 2". Until the discovery and availability of Interleukin 2 and the establishment of new culture and cell separation techniques it was difficult to obtain from a tumor patient or a suitable i.e., immunologically compatible donor, large quantities of immunologically active cells from the tumor patient (or from a single individual) which are particularly active in killing or inactivating tumors. Only recently have clinical investigators begun investigating sufficient and correct means and methods for positioning said cells in the body and maximizing their effectiveness against tumors.

SUMMARY OF THE INVENTION

It is an object of this invention to provide a method of treating mammals having cancerous tumors in vivo, which method is helpful to kill and/or inactivate the tumors without serious side effects to the living host.

It is a further object of this invention to provide a means in accordance with the preceeding object which is also useful to heal viral lesions in the body.

Still another object of this invention is to provide a means for delivering the cells and positioning them within the body of an individual to be treated, which means acts as a biocompatible holding matrix for immunologically active cells.

Still another object of this invention is to provide a means and method for preparing effector cells which are immunologically active in the body preferably of the patient from which they were obtained or in an immunologically compatible recipient.

According to the invention a patient having a cancerous tumor is treated by defining one or more areas occupied by the tumor. Immunologically activated cells which are antagonistic to the tumor, i.e., they kill or inactivate the tumor, are carried by a body implantable supporting matrix which is then implanted in the area defined. The matrix being biocompatible supports the cells and allows the cells to direct their immunological activity against the tumor in tumorous areas occupied by or reachable from the matrix.

Preferably the tumor or a portion thereof is first excised from the body. The matrix, which is preferably a deformable or flexible, semi-solid, meshwork or other supporting substance from which active effector cells can migrate, is surgically implanted in the area. Other immunologically active agents can be implanted in the matrix along with the immunologically active cells, as for example, Interleukin 2, other Lymphokines, hormones, polypeptides and antibodies to aid in promoting the effect of an antibody dependent cytotoxic lymphocytes.

The treatment product or system of this invention which is preferred for use in the method of this invention is in the form of a clot derived from platelet containing blood plasma carrying the tumor patient's own immunologically active cells antagonistic to a tumor. Preferably the cells in the clot are present in an amount of from about $1 \times 10^8$ to $1 \times 10^{12}$ and preferably $1 \times 10^9$ cells. The treatment product is also useful for aiding in the healing of viral lesions when administered to the body at the same dosage levels as for treating tumors.

The immunologically active cells are prepared in large numbers for use in the treatment of cancer or for treating viral lesions by isolating a cell population of immunologically active body cells having potential or actual antitumor immunological activity. The cells are first stimulated by exposure to a mitogen, tumor antigen or other agent then cultured in the presence of serum and one or more lymphokines while maintaining cells during logarithmic or expansion stage of growth at a density of from about $1 \times 10^4$ to $5 \times 10^5$ cells/ml. Preferably the primary lymphokine is Interleukin 2 and the cells are expanded to a population of from about $1 \times 10^8$ to about $1 \times 10^{12}$ cells.

It is a feature of this invention that the preferred article is a biocompatible matrix which carries immunologically active white blood cells and is in a semi-solid or solid form. This acts to aid in positioning and maintaining the cells in proper place in the body to provide activity at a desired site over a long period of time. When a clot is used, the clot provides nutrition to the cells and permits their migration out of the clot for antitumor activity. The use of the matrix is important no matter what the type of immunologically active cells selected are used, although cells prepared as effector cells in accordance with preferred preparation method of this invention have been found to be particularly desirable.

DESCRIPTION OF PREFERRED EMBODIMENTS

The biocompatible implantable matrix of this invention is nontoxic to the body preferably providing a support for physically maintaining the cells in position. In some cases, the matrix can be provided with means for nourishing the cells as well as physically supporting the cells. Suitable biocompatible support matrixes include clotted blood or plasma, collagens, gelatins such as Gel Foam a trademark of Upjohn Company, other polymers, honeycomb-like materials and other implantable biocompatible matrix materials from which active effector cells can migrate. Preferably the matrix is an autologous platelet containing plasma clot which can be augmented with antitumor effector cells.

Other materials can be added to the clot or other matrix for release in the body to help maintain the immunologically active cells and/or to aid in the treatment of the body. Such materials include but are not limited to Interleukin 2, Interferon, other lymphokines, hormones, polypeptides, antibodies and the like.

Multiple clots may be used in place of a single clot when this is more convenient, more easily manipulated or otherwise advantageous.

The invention utilizes a method for preparing highly stimulated, proliferating, effector cells in large number by culturing certain resting (non-dividing) mononuclear white blood cells. In the case of marrow and lymphopoietic tissue the cells may not have to be rapidly proliferating providing sufficient numbers of progenitor cells are present and are supplied with requisite lymphokines and other regulatory molecules. Preferably the white cells are from the blood of the cancer patients him(her)self, and are expanded in the laboratory to produce hundreds of millions to billions of cells that can attack and destroy the patients own cancer cells.

The culture medium can contain a specific growth factor such as Interleukin 2 to sustain rapid cell growth and augment the cells' anticancer effectiveness. It may also contain additional stimulating substances such as cytokines, hormones, polypeptides, tumor antigens, antibodies and stimulants or mitogens such as phytohemagglutinin (PHA) and concavalin A.

The cells can be prepared for implantation by suspending them in a clot or multiple clots of the patients fresh clotted plasma. The clots are placed in a tumor bed after surgical removal of the tumor or injected or otherwise introduced into the tumor subcutaneously. The clot or clots serve as a depot from which the active mobile effector cells can migrate into surrounding tissue to seek out and destroy cancer cells in the surrounding tissue. The clot acts to provide nutrients for the cells and may contain stores of IL2 or other substances as previously described to prolong the survival and maintain stimulation of the implanted cells. The cells and matrix can be administered by syringe or by physical implantation in the body in the tumor area to be treated before or after a portion of the tumor is first removed or into the tumor mass without reducing it surgically. The cells implanted in the body may also be delivered to tumor area from a remote implantable "reservoir" with a delivery port in the tumor or tumor area. Rigorous sterile techniques are used when implanting the cells and matrix in the body.

The cells which can be carried by the implantable matrix include any immunologically active cells which are antagonistic to tumors. Such effector cells include natural killer cells, null cells, macrophages, cytotoxic T cells, LAK cells and others.

In a preferred method of isolating effector cells from the body, for use in treating an individual, blood is obtained which is preferably autologous to the individual but can be any blood that can be administered without triggering destructive immunological reactions in the patient to be treated.

The cell to be treated can be obtained from blood, lymph, spleen, bone marrow or lymphatic tissue. If the cells are obtained from blood, the blood is collected in a manner that prevents coagulation or permanent entrapment of cells in a blood clot. Typically this would be done by collecting blood in an anticoagulant such as heparin, acid citrate dextrose, citrate in a sufficient amount to prevent clotting. Alternatively, the blood might be defibrinated by conventional methods or the clot in clotted blood dissolved by enzymatic action. The blood cells in suspension can be centrifuged. This allows separation of mononuclear white blood cells although other separation techniques such as sedimentation, gradient elution and the like can be used for separation. The red cells, and platelets and serum can be discarded. The mononuclear white blood cells can then be washed to remove the separating medium (if used) and put into a culture medium, as for example, for at least two (2) hours. Macrophages stick to the flask and can be collected separately or discarded with the nonstuck freely suspended mononuclear cells continued in suspension culture. The separated cells can be cultured to get a clean population of non adherent mononuclear cells which need not be a homogenous population but can be a mixture of such cells. Culture can be carried out in known culture media such as Roswell Park Memorial Institute 1640 (RPMI 1640), Delbecco's Modified Eagles Medium (DMEM) or a mixture of F12 and Delbecco's Modified Eagles Medium. Other known culture medias which including amino acids, vitamins, salts, trace metals, carbon sources such as glucose and essential trace materials can be used. The culture is preferably carried out in liquid media.

Initial exposure to mitogens is used to trigger nondividing "resting" cells into the proliferating state.

Mitogens such as concavalin A, lipopolysaccharides, tumor antigens, fetal calf serum or other mammaliam serum, Interleukin 2, Polyclone a (trademark product of Collaborative Research of Lexington, Massachusetts comprising a condition medium containing IL2 and other lymphokines with residual PHAP) can be used. After the initial exposure to a mitogenic agent, the culturing is preferably carried out in the presence of serum and a lymphokine. The IL2 used can be in the form of serum-free, mitogen-free IL2 as well as mitogen and serum containing IL2. For example, human T cell Polyclone, a trademark product of Collaborative Research of Lexington, Massachusetts can be used. That product contains conditioned media from cultures of phytohemmagglutinin-P stimulated human peripheral blood leucocytes (modified method of Alvarez et al, J of Immunol. 123:977, 1979). The activity of a typical lot of the material is $1406\frac{1}{2}$ maximal units of human T cell growth factor activity per 14 milliliters. The formulation includes minimum essential media (MEM) with 5 mg human serum albumin per ml, phytohemmagglutinan-P content is approximately 50 micrograms per ml.

Culturing is carried out while maintaining the cells in the logarithmic or expansion stage of growth at a density of from about $1 \times 10^4$ to about $5 \times 10^5$ cells per ml. Conventional temperatures such as 37° C.±1° C. can be used, as known for mammalian cell growth. Time periods of culturing can range from 24 months or higher with cells produced in volumes of from at least about $1 \times 10^8 \times 1 \times 10^{12}$ and preferably $1 \times 10^9$ cells. The Interleukin 2 used can be natural IL2 or Interleukin 2 obtained by recombinant genetic engineering techniques. Natural IL2 obtained from mammals and preferably from human blood is preferred.

In the culturing procedure, the blood, spleen or marrow tissue used to obtain the cells for culture is preferably obtained from the individual having the tumor to be treated. The cells are withdrawn from the body, prepared as monodisperse cell suspensions by established tissue culture methodology, treated and cultured in accordance with the present invention and then returned to the body as a dosage unit in the matrix materials of this invention.

It is important that the cells during the expansion stage not exceed a cell density that slows the cell proliferation rate. Typically, the upper limit of cell concentration is $10^5$/ml. Cells must be maintained in logarithmic growth or else the cells stop multiplying and large numbers of cells cannot be obtained. The cells can be maintained at the required density by adding additional media as required or removing cells as produced. When a total cell population of from $1\times10^8$ to $1\times10^{12}$ and preferably $1\times10^9$ cells has been produced, the cells can be removed from suspension by centrifugation and physically washed with physiological saline or Hanks or Earles balanced salt solution to remove mitogen, serum, lymphokines and the like. The washed cells are then suspended in fresh decalcified platelet containing plasma, preferably from the patient to be treated, after which calcium ions in the form of calcium glutonate, or calcium chloride or other forms can be added to initiate clot formation.

The clots formed are a fibrous network of interlocking proteins which give structure to the plasma and have some nutritive value. The clots support natural immunologically active cells and other treating agents which are released to effect a tumor. Clots are ultimately resorbed by the body. Some of the materials used, include hydrogels which can form useful matrixes, may remain in the body without resorbtion or may be removed by later surgical procedures if desired.

The matrix when in the form of a clot or other body absorbable substance, can be absorbable and utilized as cells perform their immunological function or can remain as "empty scaffolding" in the case of non-resorbable sheet, mesh, honeycomb type and the like.

In a specific preferred embodiment of preparing cells and treating an individual in accordance with this invention, a clot carrying immunologically active cells is formed as in Example 1 below:

EXAMPLE 1

Using sterile technique, about 50–100 ml venous blood from an individual having a brain tumor is obtained and transferred to a 150 ml flask containing 30 to 40 glass beads with the flask then being rotated in a horizontal plane until the blood is defibrinated. The blood is diluted 1:1 with sterile Hanks balance saline solution (HBSS) and layered over Ficoll-Hypaque a product of Pharmacia Fine Chemicals of Piscataway, N.J. The Ficoll Hypaque technique of Pharmacia Fine Chemicals of Piscataway, N.J. is used for in vitro isolation of the white blood cells. The diluted defibrinated blood is placed in 50 ml centrifuge tubes, centrifuged at approximately $400\times g$ for 45 minutes to yield an interface layer of predominately mononuclear cells between the plasma and the Ficoll layers. The plasma layer is aspirated and discarded. The mononuclear cell layer is aspirated, transferred to a fresh centrifuge tube, diluted 1:6 with HBSS and centrifuged at approximately $250\times g$ for 10 minutes. The supernatant is removed and discarded and the cell pellet which contains some erythrocytes is suspended in a solution containing 8.3 grams ammonium chloride, 0.02 grams disodium EDTA, 1.0 sodium bicarbonate per liter. This lysis the red cells.

The cell suspension is centrifuged and the remaining cells are washed twice with HBSS. The cells are then suspended in RPMI 1640 fortified with 10 percent fetal calf serum. To this may be added penicillin 100 micrograms and 100 micrograms streptomycin/ml or other antibiotics. The cell count at this stage is approximately $5\times10^5$ ml.

The cells are incubated in a tissue culture incubator with 5% $CO_2$ overnight to allow adherent cells to attach to the flask. The non adherent cells are transferred to a fresh flask and phytohemagglutinin (PHA) is added at a concentration of 10 micrograms per ml. The cells are incubated for about 20 hours at 37° C. in the incubator. Collaborative Research, Inc. human Interleukin 2 is added to the cells at a concentration of $15.0\frac{1}{2}$ max units per ml after the cell concentration has been adjusted to approximately $1\times10^5$ ml. After 2–3 days the medium (condition medium) is removed and part of it is used to supplement the nutrient medium when it is next changed.

The culture is maintained by adjusting cell concentration every 2–3 days to a cell concentration of about $1\times10^5$ cells per ml. When fresh medium is added it is supplemented with 10 percent (V/V) conditioned medium from the previous passage. IL2 is maintained at $15.0\frac{1}{2}$ max units/ml throughout. Fresh IL2 is added for the final 24 hours of culture. On the day of surgery, the cells are centrifuged out of their medium, washed two times with HBSS and resuspended in decalcified plasma obtained from the patient the same or previous day. The patients tumor is then excised, the plasma is recalcified with calcium ions sufficient to cause clotting, and the clot is implanted in the tumor bed.

The dosage rates to the patient can vary greatly. Preferably, a dose rate of $1\times10^9$ cells is preferred. The volume of cells to matrix can vary greatly and often is in the range of from 4 to 5 percent by volume cells and 95 to 96 percent by volume matrix with overall matrix volumes of from 20 to 25 ml volumes possible for use.

The tumors to be treated by the methods and products of this invention include malignant tumors of the brain and other areas of the body.

EXAMPLE 2

A 37 year old woman had undergone brain surgery previously at the seventh month of her pregnancy with the removal of a grade 2–3 glioma. The tumor recurred within a two to three month period following radiation therapy. She had a posterior occipito-parietal grade 3 astrocytoma at the time of surgery which was subtotally debulked. Autologous stimulated lymphocytes ($1\times10^8$ cells in approximately 25 ml of clotted plasma) prepared and treated substantially in accordance with Example 1, were implanted in the tumor cavity. Followup at 7.5 months post-operatively showed absolutely no evidence of the tumor on repeat CT scans and the patient was clinically asymptomatic at this time. When the tumor was debulked approximately 36 cc of tumor remained. CT scans taken at 1 week, 3 months and 5 months post implantation showed a decrease in tumor volume from 36 cc to 0 at 7 months.

EXAMPLE 3

A young Doberman dog had a one month history of convulsions and loss of vision in one eye. Computerized tomography (CT) and magnetic resonance imaging (MRI) scans showed a large area of localized encephalitis, probably viral in origin, in the right parietal region. Craniotomy was performed and part of the lesion removed. At surgery, $1.02\times10^8$ stimulated autologous lymphocytes embedded in a clot of the dog's own plasma were implanted in the brain in the area from which the encephalitic lesion was removed. Three weeks later the dog was free of symptoms and the CT scan showed resolution of the lesion.

While specific embodiments have been described, many variations of this invention are possible. Mononuclear cells or lymphocytes may be prepared using many existing methods for increasing the effector or immunologically active cell populations. Such cells can be labeled as with monoclonal labeling, tagged with radiological materials and the like before being implanted. Pure cell types or mixtures of known cell types can be used where there are therapeutic advantages. Cells may be administered in a clot, droplet or on or in a carrier substrate. Combinations of cell types and carriers may be designated for maximum therapeutic efficiency.

The cells may be treated before implantation so that they contain a tag substance or label that does not interfere with cell function or survival but permits monitoring by standard radiological methods such as radiograph, C.T. scanning, magnetic resonance imaging, spin resonance, P.E.T. scanning and the like.

Lymphocytes may be sensitized to a patients tumor or to antigens common to tumors of the type to be treated by culturing the lymphocytes in the presence of tumor antigens or inactivated tumor cells (killed or rendered incapable of cell division) before harvesting the lymphocyte for implantation. The immunologically active cells used are preferably autologous cells to the patients being treated although this is not required in all cases.

Generally, the mononuclear white blood cells which are the immunologically active cells, are taken from peripheral blood of a tumor bearing patient and cultured so that the cells increase in number and in anticancer effectiveness prior to being returned to the same patients tumor bed after some or most of the tumor has been removed surgically. Preferably the cells are processed on to isolate effector cells as from venous blood, which are then cultured in vitro in the presence of T cell growth factor (IL2) after initial exposure to plant lecitin PHA or other mitogen followed by final stimulation of cultured cells with fresh IL2 and possibly other stimulant molecules. The so treated and expanded cells are returned to the patient, preferably in the patient's own recalcified, clotted fresh plasma.

The invention includes as its novel points the preferred use of only non adherent mononuclear cells while excluding short lived granulocytes. The cells are cultured for approximately two (2) weeks or more in the presence of optimal concentrations of human Interleukin 2 under conditions that promote near maximal rates of cell growth (sustained logarithmic phase growth) and they are returned to the patient while in this state. Preferably the culturing time is about 2 weeks and the cells are at a count of $10^9$.

The invention exploits a known physiological mechanism mainly cellular immune response to destroy a cancer without recourse to chemotherapy or radiation therapy, except as an adjunct since those therapies can cause serious toxicity including immunosupression. The invention overcomes the difficulties that are sometimes present in patients with cancer, which difficulties include depression of the cellular immune response. It is believed that the prior problems are overcome in part because the effector cells used in the present invention are removed from the patient and from the more or less suppressive environment of the cancer bearing patient's body.

The cells are washed several times to remove as much as possible of suppressive substances that may be bound to the cells and then the cells are suspended in a tissue culture media when the cytotoxic cells selected for therapy are lymphocytes. Excessive numbers of monocytes may inhibit cytotoxic lymphocytes. For this reason, most monocytes are removed by allowing them to attach to a tissue culture flask. The non adherent cells which include a small percentage of monocytes are treated to cause a transformation from the usual resting state of the cells which is non-dividing to a synthetically active, dividing stage which expresses binding sites for Interleukin 2. Thereafter the multiplying cells are maintained under optimal culture conditions so they enter sustained log phase growth. This can result in greatly increased numbers of cells that have been rescued from many suppressive factors active in the patient, stimulation of the cell's cytotoxic (anticancer) effectiveness as a result of the mitogen and IL2. Suspending the cells in a plasma clot for implantation into the tumor bed protects and nourishes the cells and makes it possible to deliver and confine them to the tumor area where they are needed. The active cells can migrate freely out of the clot to the surrounding tissue. The clot may also contain fresh platelets which augment the antitumor effectiveness of the effector cells. No foreign toxic agents need be introduced to the body.

The treated cells and the matrix support of this invention can find use in tumor therapy as described and also in treatment of localized viral lesions. When treating viral lesions, the treated cells and matrix can be used at dosage levels and with application methods as described for tumor use. The method can result in healing of lesions caused by a wide variety of viruses in a wide variety of body locations.

What is claimed is:

1. A method of treating a patient having a tumor comprising,
    defining an area occupied by a tumor,
    introducing into said area immunologically active cells which are antagonistic to said tumor with said active cells being carried by a body implantable matrix,
    said matrix being biocompatible supporting said cells and being a clot.

2. A method in accordance with the method of claim 1 wherein said clot is an autologous clot.

3. A method in accordance with the method of claim 2 wherein said cells are antitumor white effector cells.

4. A method in accordance with the method of claim 2 wherein said clot is formed from a substance selected from the group consisting of plasma and plasma derived proteins.

5. A method in accordance with the method of claim 1 wherein said clot is formed from platelet containing plasma autologous to the patient and is augmented with said antitumor effector cell.

6. A method in accordance with the method of claim 5 wherein a portion of a tumor is removed from said area and said area is then packed with said biocompatible implantable matrix carrying said immunologically active cells to maintain said cells for treatment of said area.

7. A method of treating a patient having a tumor comprising,
    defining an area occupied by said tumor, introducing into said area immunologically active cells which are antagonistic to said tumor with said active cells being carried by a body implantable matrix,
    said cells being antitumor white effector cells and said matrix is a semi-solid to solid matrix from which active effector cells can migrate,
    said matrix being biocompatible and supporting said cells.

* * * * *